July 2, 1946. P. J. SCHMIDT Plant Pat. 705
BUDDLEIA PLANT
Filed Nov. 9, 1945
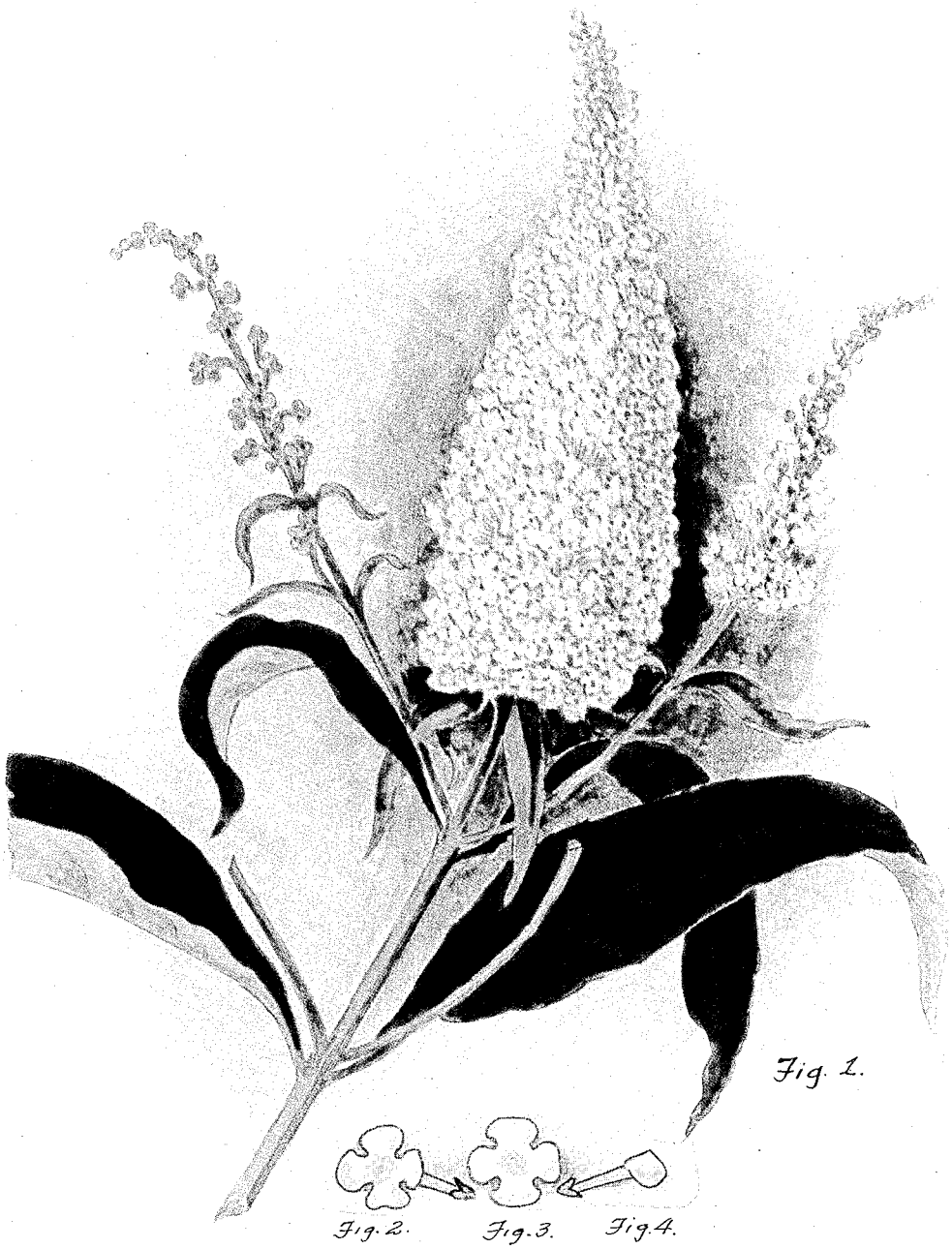
WITNESS
Addison E. Avery
INVENTOR.
Paul J. Schmidt,
ATTORNEY.
John H. Bernard Patented July 2, 1946

Plant Pat. 705

UNITED STATES PATENT OFFICE

705

BUDDLEIA PLANT

Paul J. Schmidt, Youngstown, Ohio, assignor to The Wayside Gardens Company, Mentor, Ohio, a corporation of Ohio Application November 9, 1945, Serial No. 627,653

1 Claim. (Cl. 47—60)

This invention relates to a new variety of Buddleia plant.

The present Buddleia plant was produced by me by crossing a white seedling as the female or seed parent and Buddleia Orchid Beauty as the male or pollen parent, Orchid Beauty being a fixed commercial variety.

The white seed parent is from the cross of a white sport of Buddleia Dubonnet and a white sport of Buddleia Fortune, which is disclosed in United States Plant Patent 206.

The seeds resulting from the cross of the seed and pollen parents were planted and from the resultant plants the present variety was selected for further propagation and first asexually reproduced by root cuttings and subsequently was asexually reproduced in test fields of Wayside Gardens Company, of Mentor, Ohio, and of Paul J. Schmidt Nursery at Youngstown, Ohio.

*The drawing*

Fig. 1 is a general side elevation on a reduced scale of a part of one of the lateral branches of the plant bearing an inflorescence in full bloom with sub-laterals bearing flower buds in various stages of development, the inflorescence of the lateral branch, in addition to being on a reduced scale, being shorter relative to its diameter than is the actual inflorescence, for the purpose of showing in more detail its compact composition, its long pointed tip, large diameter, rather abrupt termination at the base and arrangement of the individual florets.

Figs. 2 and 3 are enlarged views of an individual floret viewed at an angle to the axis of the funnel and axially of the funnel, respectively; and Fig. 4 is an enlarged view of an individual floret bud viewed at an angle to the axis of the funnel.

*The plant generally*

The plant has openly branched roots of average size. It is deep rooted with a lateral spread that is usual or somewhat greater than usual for Buddleias. The roots are exceptionally resistant to disease, withstanding both wetness and drouth well, and have good winter resistance, having withstood without harm temperatures of 4° F. below zero in northern Ohio.

The plant grows well in any good soil where winter drainage is good and it needs little or no winter protection. The exposed plant is generally bushy and regular in shape and grows to a height of four to five feet with a spread of three feet.

It prefers full sun, any exposure other than a northern exposure, clay loam to slightly sandy soil which is moist but well drained. Though it will grow in very sandy soil, the inflorescences are smaller in such soils.

The main stalks grow upright and are very well branched. They are very stiff, exceptionally straight and support the flower heads well and without drooping so that no external supports are required to maintain the plant in a neat and regular form. They are generally uniform in color, being a green, comparable to Maerz and Paul Plate 20–K–3 through 20–K–5. The main stalks vary in length from forty-eight to seventy-two inches on the average, rising from the roots in groups and being oppositely branched. The branches are straight and stiff and uniform in color, being of approximately the same green as the stalks above described.

The foliage is compact with oppositely arranged leaves in abundance. The leaves are green comparable to Maerz and Paul Plate 23–J–1 through 23–J–5, on the upper surface and silvery green comparable to Maerz and Paul Plate 20–A–2 on the under surface. The leaves are exceptionally long and pointed and of average thickness. Many leaves near the base of the plant are eight inches in length and from one and three-quarters to two inches wide at their widest part. They are smooth on the upper face and fuzzy on the under face. The leaves are progressively narrower in proportion as the upper part of the plant is approached.

The flowering is affected by the usual factors, the best blooms being obtained in a sunny exposure other than northern, in well drained neutral soil of average moisture. Too much shade produces small flower heads of poorer quality. Poor sandy and rocky soils produce flowers which are good but are small in size. The blooming period generally is from July until frost comes, usually in October. The plant blooms continuously during this period.

The inflorescences or flower heads are very large, ranging from two to three inches in diameter and from twelve to eighteen inches in length on the main stalks and being of about the same diameter but usually averaging an inch or so shorter on the main laterals. The inflorescences usually are of substantially uniform diameter from the base to the longitudinal midportion or to a point well above the base where the taper of the tip begins. Usually this uniform diameter portion is about two thirds of the length of the inflorescence, the remainder being uniformly tapered to the very sharp tip. In some instances there is a very slight taper between the base and the beginning of this more pronounced taper but the beginning of the latter is very apparent. Because of its large size and great length, the fully blooming inflorescence, shown in Fig. 1, is not only on a reduced scale but has been shortened disproportionately in length relative to diameter, as otherwise the arrangement and appearance of the florets in the head as a whole and their compact arrangement could not be shown adequately. This shortening has been accomplished mostly by reducing the length of the lower two thirds or uniform diameter portion of the inflorescence. The long tapering sharp tip is a predominant feature of the inflorescence and consequently the shortening in Fig. 1 has been obtained by reducing the length of the longitudinal mid-portion which is of substantially the same diameter throughout its length.

The flower heads are filled out well entirely around the stem and are straight and borne upright without any perceptible droop. In fact, the axis of the terminal flower head of each stalk entirely to its tip is a continuation, without any break or appreciable curvature, of the axis of the straight uncurved main stalks, and the axis of the flower heads of the lateral and sub-lateral branches likewise are continuations of the axes of their supporting branches, without appreciable break or curvature.

An average of fifty or more inflorescences or flower heads are borne on a single plant. The permanency of the blooms is very good. Most blooms remain in good condition for a week on the plant and for a period of three to four days when cut. The florets are about the same size as those of the Buddleia Fortune but are much longer than other white Buddleias. Their color is distinctive. The petals are pure white. Each floret has an orange eye comparable to Maerz and Paul Plate 9–L–6 through 9–L–8 and the tubes have a general color comparable to Maerz and Paul Plate 12–A–9 through 12–E–9. The florets bloom gradually from base to tip, those first blooming remaining in good condition until well after the entire flower head is in bloom. The bloom has a pleasing fragrance.

The plant is characterized particularly in the purity of the whiteness of the florets and of the inflorescence as a whole; the compact arrangement of the florets entirely around the central stem and resultant well rounded flower heads, the large size and long pointed tips of the flower heads; the large size of the florets for a white Buddleia; the unusual height of the plant which is comparable to that of colored Buddleias, the permanence of the blooms when cut which make it very desirable as a cut flower, the straight, stiff well branched long stem, and the bearing of the flower heads thereon without perceptible break or curvature from the base of the stalk or branch entirely through to the tip of the heads.

I claim:

The new and distinct variety of Buddleia plant herein shown and described and characterized particularly in large, well rounded, and sharp pointed flower heads, the purity of the whiteness of the florets and flower heads, the permanence of the blooms when cut, the long, straight, well branched stiff stalks, and the bearing of the flower heads on the stalk or branches without break or curvature.

PAUL J. SCHMIDT.